United States Patent [19]
Collins

[11] 3,983,755
[45] Oct. 5, 1976

[54] MOLTEN METAL SAMPLER
[76] Inventor: William J. Collins, 7005 Madison St., Merrillville, Ind. 46410
[22] Filed: Mar. 31, 1975
[21] Appl. No.: 563,581

[52] U.S. Cl. .......................... 73/425.4 R; 249/111; 249/DIG. 4
[51] Int. Cl.² ........................................ G01N 1/12
[58] Field of Search ................. 73/DIG. 9, 425.4; 249/111, DIG. 4; 164/4

[56] References Cited
UNITED STATES PATENTS
3,315,529   4/1967   Feichtinger .................. 73/421.5
3,415,124   12/1968  Collins ......................... 73/425.4

FOREIGN PATENTS OR APPLICATIONS
406,676   8/1966   Switzerland ................... 73/DIG. 9

Primary Examiner—S. Clement Swisher

[57] ABSTRACT

The invention involves providing a molten metal sampler or device with means for dissipating heat therefrom when the sample is obtained.

18 Claims, 8 Drawing Figures

MOLTEN METAL SAMPLER

BACKGROUND

The purpose of providing the sampler or device with means for dissipating or radiating heat therefrom is to obtain a superior resultant sample for analysis.

More particularly in this regard the object is to increase the external area of half sections of the device which define a chamber or cavity for receiving the molten metal whereby to promote or expedite radiation of heat away from the sections and thereby obtain a more rapid cooling and solidification of the molten metal in the chamber and impart to the sample what may be characterized as crystaline chill surfaces which offer advantages with respect to spectographic or X-Ray quantitative determination. Otherwise expressed, the chill surfaces obtained are considered to contribute to a better sample for analysis as compared to those which are obtained from a device which is not provided with heat dissipating means.

OBJECTIVES

In view of the foregoing, one of the important objects of the subject invention is to provide a device which comprises a pair of half sections having channel or grooved extended portions which when assembled form a primary chamber for receiving a sample of molten metal and a tubular formation, and the half sections are provided with means for dissipating or transmitting heat from the sections for the purpose of substantially instantly cooling the sample to obtain a more uniform density thereof for analysis.

The half sections include enlarged head portions which are recessed to provide the primary chamber and external side surfaces or area of the head portions are provided with the heat dissipating means.

More particularly, such means may be designed and constructed in various ways but as disclosed herein it is preferably in the form of what may be termed serrations, fins, dimples, pimples, indentations, projections or grooves which may be of variable shapes whereby to appreciably increase the external areas or surfaces of the half sections and particularly the external side surfaces of the head portions. Such means, if so desired, may be in the form of fins or ribs which extend or project outwardly from the regular external surfaces of the sections.

A significant object of the invention is to provide a setup whereby, if so desired, edge portions of the head portions may be provided with grooves or fins whereby to augment the cooling of the head portions.

Also, an object is to provide half sections, in which the channel or extended portions thereof may, if so desired, be provided with heat dissipating means.

A further object of the invention is to provide a device having half sections which are constructed of a frangible material and provided with means which serves the dual purpose of dissipating heat therefrom and facilitate breakage of the sections after a sample has been obtained.

A specific object of the invention is to provide the channel or extended portions of the half sections with grooves or ribs which may also serve to assist in holding a casing or sleeve about the extended portions for at least partially maintaining the sections assembled.

Additional objects and advantages of the invention will become apparent after the description hereinafter set forth is considered in conjunction with the drawings annexed hereto.

Reference is made to Applicant's copending applications Ser. Nos. 543,687, 563,590, 595,155, and 690,296 which disclose and/or claim broader aspects of one or more secondary chambers for receiving molten material for analysis.

Figure 3:
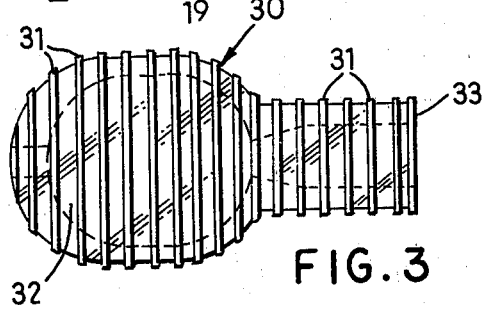
FIG. 3 is a top view of one of a pair of half sections of a subassembly of a device provided with heat dissipating means of a character different from that shown in FIG. 1.
Figure 4:
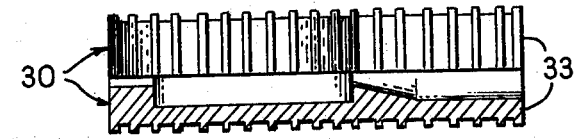
FIG. 4 is a partial longitudinal section of the subassembly shown in FIG. 3.
Figure 5:
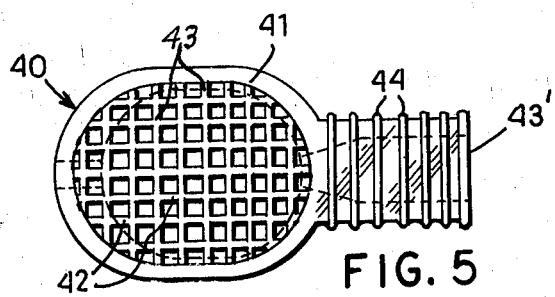
Figure 6:
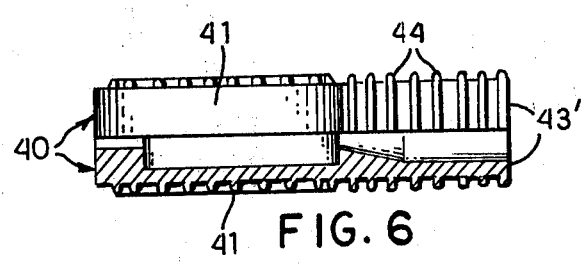
Figure 7:
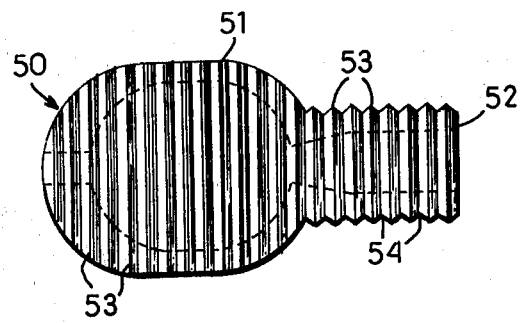
Figure 8:
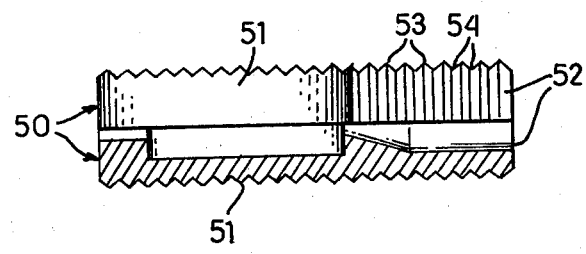

FIGS. 5 and 6 are views which are respectively similar to FIGS. 3 and 4 and disclose a modified form of heat dissipating means; and FIGS. 7 and 8 are views which are respectively similar to FIGS. 3 and 4 and 7 and 8 and disclose another modified form of heat dissipating means.

DESCRIPTION

The general aspects or structure of a device will be described prior to that of the means utilized for dissipating or radiating heat therefrom.

Figure 1:
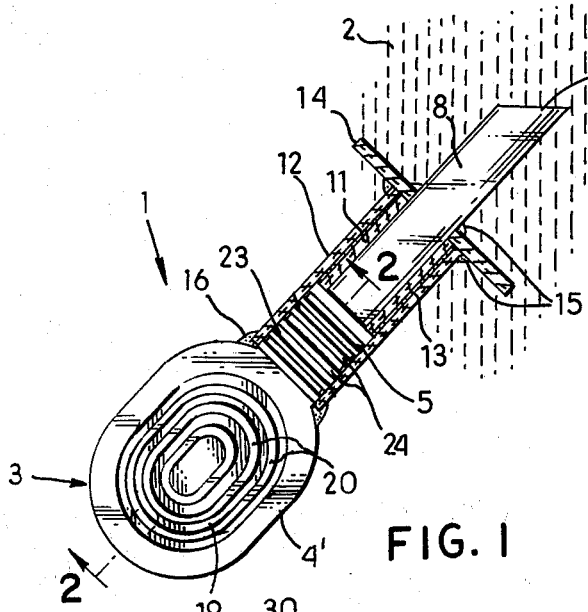
FIG. 1 is an elevational view showing a device disposed in a stream of molten metal for obtaining a sample therefrom, including heat dissipating means provided on portions of the device.
Figure 2:
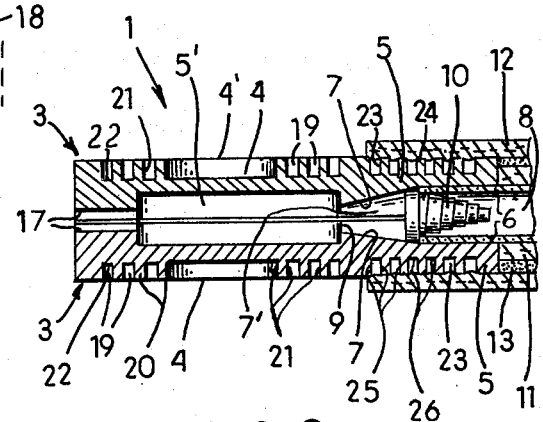
FIG. 2 is a longitudinal section taken substantially on line 2—2 of FIG. 1 illustrating structural details of the device.

Referring to FIGS. 1 and 2 there is illustrated a device generally designated 1 which is disposed in relation to a stream of molten metal 2 for obtaining a sample therefrom.

More particularly, the device 1 preferably comprises a pair of half sections generally designated 3 constructed of molded powdered metal and having enlarged recessed or head portions 4 and extended channel portions 5 which when correctly assembled provide a primary oblong chamber 5' for receiving a sample of molten metal from the stream or some other source, and a tubular formation. Each of the channel portions is provided with a semicylindrical groove 6, a tapered groove 7, which pairs of grooves in combination respectively form a cylindrical opening for accommodating an inner extremity of a tubular means or tube 8 of Pyrex, quartz, or other suitable material, and what may be termed a mixing, tapered, or intermediate chamber 7' which converges toward the primary chamber and communicates therewith through an entrance or passage 9.

A deoxidizing means 10 of a coiled conical character is preferably arranged in the device and its inner or larger portion is preferably held against the tapered surface or surfaces of the grooves 7, forming the tapered chamber 7' by the inner end of the tube 8 and that the remainder of the coil extends forwardly in the tube as shown. With this setup the molten metal flowing into the device will substantially instantaneously melt and diffuse the deoxidizing means for infusion into the metal for deoxidizing or conditioning it substantially in the chamber 7' prior to its flow into the primary chamber via the passage 9.

The device also preferably includes a sleeve 11 which is disposed about the tube 8 in abutting relation with the ends of the channel portions 5 and an outer casing 12 which surrounds the channel portions 5, sleeve 11 and the tube 8 whereby to assist in maintaining these components assembled. Cement 13 may be interposed between the sleeve and tube whereby to additionally assist in holding the components assembled.

A shield 14 is preferably utilized to prevent any inflow between the outer ends of the sleeve and tube and also divert splashing of molten metal away from an operator. The sleeve, casing and shield may be made from any material suitable for the purpose but are preferably made of a resilient material such as pasteboard and the sleeve and casing are also preferably constructed to have a square or rectangular cross-section but if desired, they may be made round or otherwise. The shield is square and of uniform in thickness, provided with a center opening through which the tube extends and is preferably held in abutting relation with the outer flush ends of the sleeve and casing by cement at various locations, such as indicated at 15, and also at 16 at the junction between the inner end of the casing and the head portions of the half sections whereby to also assist in holding the head portions together.

Attention is directed to the fact that each of the head portions may be provided with an axial groove 17 which grooves in combination define a secondary chamber which receives molten metal from the primary chamber whereby a sample portion of a predetermined weight, such as one gram, when severed may be obtained for analysis in addition to portions formed in the primary chamber 5, tapered chamber 7' and in the tube 8 for analysis, after the components are disassembled or broken apart. The head portions are also preferably provided with projections nesting in notches (not shown) whereby to assist in locating the sections with respect to one another during assembly and provide vents between the sections to facilitate entry of molten metal into the device through a bevelled entrance or inlet 18 provided at the tip of the tube 8.

Referring more particularly now to the invention embodied in the device 1 described above, the heat dissipating means utilized in conjunction with the device serves to increase the external area of the half sections and this is accomplished by providing the external planar parallel side surfaces 4' of the head portions 4 with means, such as a plurality of generally oblong or generally oval concentrically arranged grooves 19 of corresponding depth forming corresponding ribs 20. Each groove is defined by a pair of inset opposed parallel surfaces 21 and a bottom or inner surface 22. The surfaces 21 also constitute side surfaces of the ribs 20. With this setup the surfaces 21 and 22 appreciably increase the external side areas of the head portions. It should be noted that the grooves 19 are inset with reference to the side surfaces 4' of the head portions and that the outer surfaces of the ribs are in the same plane as the surfaces 4'. It should also be noted that the area taken up by the grooves and ribs substantially corresponds to or is greater than that of the widest cross-dimensions of the primary chamber so as to insure that all of the metal received in the device is influenced or derives the full benefit of such areas whereby to achieve expeditious cooling by radiating heat away from the device.

The channel portions 5 of the half sections are preferably provided with means, such as transverse parallel grooves 23 forming parallel ribs 24 and each groove is defined by a pair of parallel surfaces 25 and an inner or bottom surface 26. The surfaces 25 also constitute side surfaces of the ribs 24. The surfaces 25 and 26 including the outer surfaces of the channel portions also serve to promote radiating heat away from the molten metal flowing through the tube 8 and tapered or mixing chamber 7' formed by the surfaces 7.

Of particular significance is the fact that the half sections are constructed of a frangible material and that the grooves and ribs provided thereon or therein may be termed serrations and that they also serve to facilitate breakage of the sections, if required, to obtain a solidified sample therefrom.

Attention is directed to the important fact that the means constituting the grooves 23 and ribs 24 also serve to more or less lock or secure the casing 12 about the channel portions 5 of the half sections. This is accomplished by predetermining the outside cross-dimensions of the tubular formation formed by the channel portions and the inside cross-dimension of the casing so that a force of sufficient magnitude is required to telescope the casing about the channel portions to cause portions of the casing to intimately engage or recede into the grooves 23 and thereby more or less automatically lock the sleeve in place or otherwise secure a tight embracing grip upon the channel portions. In other words, the means serve a dual purpose.

In view of the foregoing it should be manifest that substantially all of the external side surfaces of the head portions 4 and the channel portions 5 are provided with heat dissipating means which increases the area of such surfaces to expedite cooling of the sample of metal obtained. As stated above, after a sample of metal has solidified the components of the device may be separated or broken away to obtain the sample for analysis.

As alluded to above, a device may be provided with various forms of heat dissipating means and some of these are exemplified in FIGS. 3 through 8.

In FIG. 4 there is illustrated a pair of half sections 30 adapted for use with additional components which correspond to or are different from those shown in FIGS. 1 and 2 to constitute a complete device for use in obtaining a sample of molten metal from a stream or other source. FIG. 3 shows a top view of one of the pair of sections of FIG. 4.

More specifically, each of the sections 30 is provided with parallel transverse serrations, ribs, or fins 31 which project outwardly from head portions 32 and channel portions 33 thereof, as distinguished from the half sections, above described, in which the outer surfaces of the ribs are disposed in the same planes as the major external surfaces of the sections. It should be noted that the heat dissipating means embodied in the half sections 30 also extend across their respective edge portions so that it may be stated that the means substantially surrounds the sections as distinguished from placement of means in the areas shown in device 1.

In FIG. 6, there is depicted a pair of sections generally designated 40 and FIG. 5, is a top view of one of the sections showing heat dissipating means of a generally waffle-like or criss-cross character or design which is applied to the opposite face sides of head portions 41 of the sections.

More specifically, the heat dissipating means comprises a plurality of parallel longitudinal outwardly extending ribs 42 and a plurality of parallel transverse outwardly extending ribs 43 which cross or intersect the ribs 42. The sections 40 also include channel portions 43' and these are provided with parallel transverse ribs 44. It should be manifest that the surfaces forming the ribs serve to increase the external surface area of the head portions of the half sections in addition to the intervening areas between the ribs to promote heat dissipation and thereby expedite cooling of a sample when received in a primary chamber 45.

In FIG. 8 there is exemplified a pair of half sections generally designated 50, and FIG. 7 is a top view of one of the sections. These sections have head portions 51 and channel portions 52 and they are provided with heat dissipating means in the form of parallel transverse pointed ribs 53 and V-shaped grooves 54. The converging surfaces of these grooves and ribs serve to increase the surface areas of the sections whereby to promote radiation of heat away from the sections as compared to sections in which the faces thereof are only of a planar character.

SUMMARY

In view of the foregoing it should be readily apparent that the half sections of a device may be provided with any of the various forms of heat dissipating means as exemplified herein and if so desired the half sections may be provided with such means which are of a different design or construction.

It is to be understood that the half sections of FIGS. 3 through 8 are in fact modifications of the half sections of FIGS. 1 and 2. In other words, it is intended that the half sections of FIGS. 3 through 8 are components adapted for use in the complete sampler device.

It is to be understood that the shapes of the half sections may be other than those shown. For example, the head portions may be round in lieu of being generally oval or oblong as shown and that the internal structure and other components such as the tube 8, sleeve 11, casing 12, and deoxidizer 10 may be constructed and assembled in ways other than disclosed.

Attention is particularly directed to the important fact that the heat dissipating means is also of such a character that it may serve to facilitate breakage of the half sections if such is required in obtaining a sample.

Having thus described my invention, it is obvious that various modifications may be made in the same without departing from the spirit of the invention and therefore, I do not wish to be understood as limiting myself to the exact forms, constructions, arrangements, and combinations of components herein shown and described.

I claim:

1. A wall structure forming a chamber for receiving a sample of molten metal, tubular means extending from said wall structure for receiving the molten metal for flow into said chamber, and groove means provided on said wall structure for dissipating heat therefrom when molten metal is being received in said chamber.

2. A subassembly for use as components of a device for obtaining a sample of molten metal, said subassembly comprising a pair of half sections having portions provided with recesses whereby when the sections are assembled the recesses define a chamber for receiving a sample of molten metal, and external groove and fin means provided on said portions whereby to dissipate heat therefrom when a sample is received in the chamber.

3. The subassembly defined in claim 2, in which said sections also define a secondary chamber for receiving molten metal of a predetermined amount, and said means also serves to dissipate heat from said secondary chamber.

4. The subassembly defined in claim 2, in which at least some of said groove and fin extend transversely with respect to one another.

5. The subassembly defined in claim 2, in which said sections are constructed of a frangible material, and said external means also serves to facilitate breakage of the sections after a solidified sample of metal is received and formed in the chamber.

6. A device for sampling molten metal comprising a pair of half sections having recessed head portions and channel portions which when assembled form a chamber and a tubular formation, said channel portions being provided with external serrations, a tubular casing of resilient material held in surrounding relation to said channel portions by said serrations, and a tube having an inner extremity held in relation to said tubular formation and having an outer extremity provided with an entrance for initially receiving molten metal for flow through said tube into said chamber.

7. The device defined in claim 6, in which said serrations also serve to dissipate heat away from the device when a sample of a metal is obtained or is being obtained.

8. A subassembly of a device for sampling molten metal comprising a pair of half sections having recessed head portions and channel portions which when assembled form a chamber and a tubular formation, said channel portions being provided with external transverse rib means, and a tubular casing of resilient material held in a surrounding relation to said channel portions by said means.

9. The subassembly defined in claim 8, in which said means also serves to dissipate heat away from the device when a sample of a metal is obtained or is being obtained.

10. A subassembly for use as components of a device for obtaining a sample of molten metal, said assembly comprising a pair of frangible half sections having portions provided with recesses and with channel portions which when assembled form a chamber for receiving molten metal and a tubular formation adapted to have a tube disposed in relation thereto for initially receiving molten metal for flow into the chamber, and said portions provided with said recesses being provided with external grooves means for increasing the external surface areas thereof whereby to dissipate heat from the sections when molten metal is received in the chamber.

11. A wall structure forming a chamber for receiving a sample of molten metal, tubular means for receiving the molten metal for flow into said chamber, and external integral ribs provided on said wall structure for dissipating heat therefrom when molten metal is being received in said chamber.

12. A wall structure forming a chamber provided with an entrance for receiving a sample of extremely hot liquid for flow into the chamber, and said wall structure being provided with means comprising indentations and integral projections for dissipating heat from said chamber when the liquid is received therein.

13. The wall structure defined in claim 12, in which certain of said indentations and projections form a waffle-like area.

14. The wall structure defined in claim 12, in which certain of said indentations and projections are of an endless character.

15. The wall structure defined in claim 12, in which said wall structure also forms a secondary chamber and a chamber intermediate said secondary chamber and said first-mentioned chamber, and said means also serves to dissipate heat from said intermediate and secondary chambers.

16. The device defined in claim 6, in which the entrance of said tube is formed to facilitate entry of the molten metal therein.

17. The device defined in claim 6, including a sleeve surrounding said tube and said casing surrounds said sleeve.

18. The device defined in claim 6, including a sleeve which surrounds a portion of said tube, said casing surrounds said sleeve, and a shield surrounds a portion of said tube, and means for holding said shield in relation to said casing and sleeve.

* * * * *